(12) United States Patent
Erben et al.

(10) Patent No.: US 7,214,475 B2
(45) Date of Patent: May 8, 2007

(54) COMPOUND FOR OPTICAL MATERIALS AND METHODS OF FABRICATION

(76) Inventors: Christoph Georg Erben, 42 Heather Dr., Clifton Park, NY (US) 12065; Eric Michael Breitung, 906 Park Ave., Apt. 2, Albany, NY (US) 12208; Ryo Tamaki, 1901 Lookout La., Clifton Park, NY (US) 12065

( * ) Notice: Subject to any disclaimer, the term of this patent is extended or adjusted under 35 U.S.C. 154(b) by 499 days.

(21) Appl. No.: 10/812,191

(22) Filed: Mar. 29, 2004

(65) Prior Publication Data

US 2005/0214479 A1   Sep. 29, 2005

(51) Int. Cl.
*G03C 5/00* (2006.01)
*C09K 19/52* (2006.01)

(52) U.S. Cl. .................. 430/326; 430/290; 430/321; 252/299.01

(58) Field of Classification Search ........... 252/299.01; 430/321, 326, 290
See application file for complete search history.

(56) References Cited

U.S. PATENT DOCUMENTS

| | | |
|---|---|---|
| 5,023,380 A | 6/1991 | Babb et al. |
| 5,402,514 A | 3/1995 | Booth et al. |
| 2003/0162985 A1 | 8/2003 | Rantala et al. |
| 2003/0166953 A1 | 9/2003 | Rantala et al. |
| 2003/0166954 A1 | 9/2003 | Rantala et al. |
| 2003/0171607 A1 | 9/2003 | Rantala et al. |
| 2003/0176718 A1 | 9/2003 | Rantala et al. |

FOREIGN PATENT DOCUMENTS

| | | |
|---|---|---|
| WO | WO 03/057702 A2 | 7/2003 |
| WO | WO 03/057702 A3 | 7/2003 |
| WO | WO 03/057703 A1 | 7/2003 |
| WO | WO 03/059990 A1 | 7/2003 |

OTHER PUBLICATIONS

H. Shah, et al, "Direct generation of optical diffractive elements in perfluorocyclobutane (PFCB) polymers by soft lithography", IEEE Photonics Technology Letters, vol. 12, No. 12, Dec. 2000, pp. 1650-1652.
D.W. Smith Jr., et al., "Perfluorocyclobutane (PFCB) polyaryl ethers: versatile coating materials", Journal of Flourine Chemistry, 104, 2000, pp. 109-117.
D.W. Smith Jr., et al, "Perfluorocyclobutyl copolymers for microphotonics", Advanced Materials, 14, No. 21 2002, pp. 1585-1589.
W. Zhou, et al, "Perfluorocyclobutyl (PFCB) copolymers containing polyhedral oligomeric silsequioxanes (POSS) for potential optical application", Polymer Preprints, 44(1), 2003, pp. 923.
XP002333093, Zhou et al., "Perfluorocyclobutyl (PFCB) Copolymers Containing Polyhedral Oligomeric Silsesquioxanes (POSS) for Potential Optical Application", Retrieved from SIN Database Accession No. 2003:211183 Abstract & Polymer Preprints, American Chemical Society, Division of Polymer Chemistry, vol. 44 (1), 2 pages, 2003.
XP002332342, Jiang et al., "Perfluorocyclobutane-Based Arylamine Hole-Transporting Materials for Organic and Polymer Light-Emitting Diodes", Advanced Functional Materials, vol. 12, No. 11-12, pp. 745-751, 2002.
XP002332343, Liu et al., "Triarylamine-Containing Poly(perfluorocyclobutane) As Hole-Transporting material for Polymer Light-Emitting Diodes", Macromolecules, vol. 33, pp. 3514-3517, 2000.
International Search Report dated May 7, 2005.

*Primary Examiner*—Geraldina Visconti

(57) ABSTRACT

A polycyclic or monocyclic perfluorovinyl compound comprising at least one structural unit selected from the group consisting of formula I and formula II

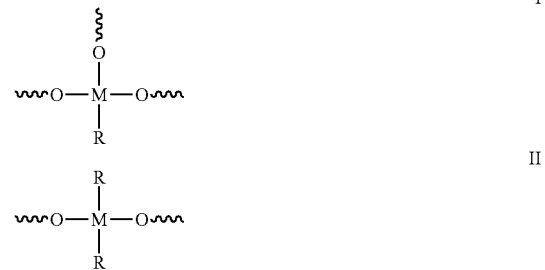

wherein M is independently at each occurrence a metal selected from group 14 of the periodic table of the elements; and R is independently at each occurrence a bond, a hydrogen, an aliphatic group, a cycloaliphatic group, or an aromatic group. The polycyclic or monocyclic compound comprises at least two perfluorovinyl groups. A method for making an optical film of the disclosed compound, an electro-optical device comprising a polymer fabricated from the disclosed compound and a polymer fabricated from the disclosed compound are also provided.

17 Claims, No Drawings

COMPOUND FOR OPTICAL MATERIALS AND METHODS OF FABRICATION

BACKGROUND OF INVENTION

This invention relates to optical materials, devices, and methods of fabrication.

Optical materials used in optical devices such as optical fibers and optical waveguides are widely used in electronics and communication to transmit data and signal over large geographic distances and variations in terrain. Optical materials are also used in signaling devices and in computer communication for shorter range data transfer. Selective design and choice of optical fiber and optical cladding materials ensures a high fidelity signal, low optical loss (or loss of signal) and a desired long life. Optical waveguide devices make use of the ability to control the pathway a beam of light follows by controlling the refractive indices of the materials used. Optical waveguide materials are increasingly required in many optical focusing, spreading, bending and transmitting applications.

Optical waveguide materials have been conventionally made from a variety of materials such as quartz, glass, acrylates, epoxies and transparent plastics and complex polymers. Silica based materials have been found potentially useful for applications where low optical loss is desired but these materials are typically expensive to manufacture.

What is needed is a cost effective method using an optical material with low optical loss to form an optical device. What is also needed is improved reliability and thermal stability in the optical material.

BRIEF DESCRIPTION OF THE INVENTION

One aspect of the present invention is a polycyclic or monocyclic perfluorovinyl compound comprising at least one structural unit selected from the group consisting of formula I and formula II

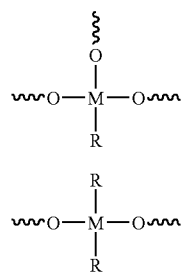

wherein M is independently at each occurrence a metal selected from group 14 of the periodic table of the elements; and R is independently at each occurrence a bond, a hydrogen, an aliphatic group, a cycloaliphatic group, or an aromatic group. The polycyclic or monocyclic compound comprises at least two perfluorovinyl groups.

A second aspect of the invention is a method of forming an optical film of the disclosed polycyclic or monocyclic perfluorovinyl compound. The method comprises providing a blend of monomer A and monomer B. Monomer A comprises a polycyclic or monocyclic perfluorovinyl compound that comprises at least one structural unit selected from the group consisting of formula I and formula II

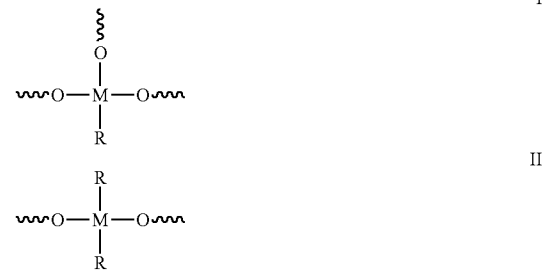

where M is independently at each occurrence a metal selected from group 14 of the periodic table of the elements and R is independently at each occurrence a bond, a hydrogen, an aliphatic group, a cycloaliphatic group, or an aromatic group; said polycyclic or monocyclic compound comprising at least two perfluorovinyl groups. Monomer B is an organic compound comprising at least two $CF_2=CF-$ units. The method comprises providing the blend, mixing the blend with a photo-initiator and a photo-curable monomer C, where the photo-curable monomer C comprises at least one of an acrylate, an epoxy, a polyimide, a silicone, a vinyl compound, a carbonate, and a diene, to yield a mixed blend; partially polymerizing at least one of the blend and the mixed blend; depositing the mixed blend on a substrate to form a film; selectively exposing the film to radiation to at least partially polymerize monomer C; and curing the film.

A third aspect of the invention is an electro-optical device comprising a polymer fabricated from a polycyclic or monocyclic perfluorovinyl compound comprising at least one structural unit selected from the group consisting of formula I and formula II

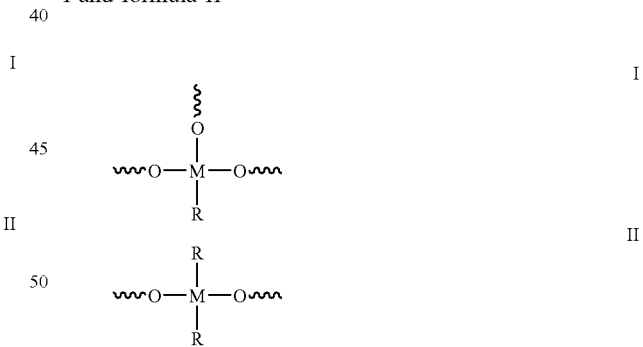

where M is independently at each occurrence a metal selected from group 14 of the periodic table of the elements; and R is independently at each occurrence a bond, a hydrogen, an aliphatic group, a cycloaliphatic group, or an aromatic group. The polycyclic or monocyclic compound comprises at least two perfluorovinyl groups.

A fourth aspect of the invention is a polymer prepared by reacting components (a), (b) and (c) wherein component (a) is a blend of monomer A and monomer B, said monomer A comprising a polycyclic or monocyclic perfluorovinyl compound comprising at least one structural unit selected from the group consisting of formula I and formula II

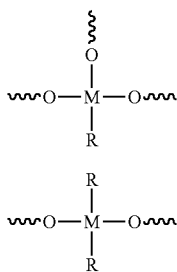

where M is independently at each occurrence a metal selected from group 14 of the periodic table of the elements, R is independently at each occurrence a bond, a hydrogen, an aliphatic group, a cycloaliphatic group, or an aromatic group. The polycyclic or monocyclic compound comprises at least two perfluorovinyl groups, monomer B is an organic compound comprising at least two $CF_2=CF-$ units, component (b) is at least one photo-curable monomer C, wherein the photo-curable monomer comprises at least one of an acrylate, an epoxy, a polyimide, a silicone, a vinyl, a carbonate, a diene, and combinations thereof and component (c) is at least one photo-initiator.

The disclosed polycyclic or monocyclic perfluorovinyl compound, method of forming an optical film, electro-active device, polymer and embodiments of the present invention may, among other applications, apply to optical waveguide systems, holograms, holographic devices, combinations thereof and to similar applications known to one reasonably skilled in the art. These and other aspects, advantages, and salient features of the present invention will become apparent from the following detailed description, and the appended claims.

DETAILED DESCRIPTION OF THE INVENTION

Referring to the chemical structures in general, it will be understood that the representations are for the purpose of describing specific embodiments of the invention but are not intended to limit the invention thereto.

Optical waveguide materials and systems generally focus, diffuse, direct or convey optical beams or signals along a desired direction. Their effectiveness often depends on controlling the refractive index across the system, their thermal stability and their adhesion to the component upon which the waveguide materials are disposed. High thermal stability and substrate adhesion ensure continued material functionality over time. Polymers, particularly those with silicon-oxygen networks (or Si—O linkages), are well suited for optical waveguide applications as compared with conventional fused glass because such polymers are processed at lower temperatures, disposable on a variety of substrates and tailorable for optical and mechanical properties.

For waveguide applications where low optical loss is key, optical materials derived from inorganic silica or from fluorinated polymers have been found particularly suited. One problem associated with conventionally synthesized fluoropolymers is relatively low adhesion to optical components or substrates, leading to device failure and limitations in operating conditions. Additionally, thermal stability in conventional fluoropolymer systems is low and leads to material degradation under fluctuating operating conditions. Conventional methods of producing an optical material using fluoropolymer do not enable the waveguide material for improved adhesion, higher thermal stability or optimal use of its low optical loss characteristics.

In one embodiment, the invention provides a compound for use as an optically graded material. In another embodiment, a method for forming an optical film is disclosed. A third embodiment provides an electro-optical device comprising an optical waveguide material. A fourth embodiment provides a polymer fabricated from the claimed compound.

One aspect of the present invention is a polycyclic or monocyclic perfluorovinyl compound comprising at least one structural unit selected from the group consisting of formula I and formula II

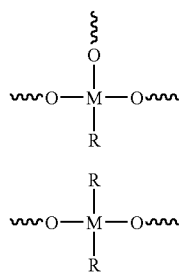

where M is independently at each occurrence a metal selected from group 14 of the periodic table of the elements; and R is independently at each occurrence a bond, a hydrogen, an aliphatic group, a cycloaliphatic group, or an aromatic group. The polycyclic or monocyclic compound comprises at least two perfluorovinyl groups.

In one embodiment of the disclosed polycyclic or monocyclic perfluorovinyl compound, the aliphatic group is an alkyl group, an alkoxy group, a perhaloalkyl group, a partially halogenated alkyl group. In another embodiment, the aromatic group is an aryl group, an aryloxy group, a perhaloaromatic group, or a partially halogenated aromatic group. In a third embodiment the perfluorovinyl compound has a formula III $$[RsiO_{3/2}]_n \qquad \text{III}$$

where R is independently at each occurrence a hydrogen, an aliphatic group, a cycloaliphatic group, or an aromatic group; and n is a number from 2 to about 1000. In a fourth embodiment, the perfluorovinyl compound has a formula IV $$[R_2SiO]_n \qquad \text{IV}$$

where R is independently at each occurrence a hydrogen, an aliphatic group, a cycloaliphatic group, or an aromatic group; and n is a number from 2 to about 1000. In a fifth embodiment, the monocyclic or polycyclic perfluorovinyl compound further comprises structural units selected from the group consisting of formula V and formula VI

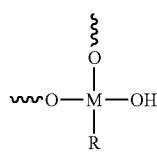

-continued

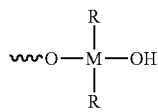
VI where M is independently at each occurrence a metal selected from group 14 of the periodic table of the elements and R is independently at each occurrence a bond, a hydrogen, an aliphatic group, a cycloaliphatic group, or an aromatic group. In one embodiment, M comprises at least one of silicon and germanium. In another embodiment, the monocyclic or polycyclic perfluorovinyl compound comprises a silicon-oxygen network. In another embodiment the silicon-oxygen network comprises an oligosilsesquioxane. In another embodiment, the oligosilsesquioxane comprises a polyhedral oligomeric silsesquioxane. In another embodiment, the polyhedral oligosilsesquioxane comprises an octahedral structure.

Silsesquioxanes are most often prepared via hydrolytic condensation reactions of trifunctional organosilicon monomers such as $RSiCl_3$ or $RSi(OMe)_3$. Many hydrolytic condensation reactions produce synthetically useful quantities of fully condensed polyhedral oligomeric silsesquioxane frameworks containing 6, 8, 10, 12 and combinations thereof of Si atoms. The silsesquioxane framework is built upon Si—O linkages and clusters.

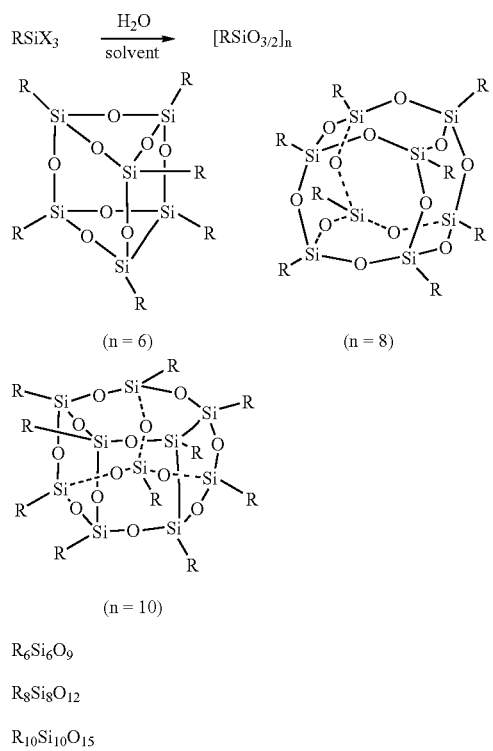

$R_6Si_6O_9$ (1)

$R_8Si_8O_{12}$ (2)

$R_{10}Si_{10}O_{15}$ (3)

Similar Si—O clusters are prepared by alkaline catalysis of tetrafunctional silicon monomers such as tetraethoxysilane $Si(OEt)_4$. Tetraethoxy silane clusters are functionalized silicates having $[(SiO_2)_n(SiO_4)_m]^{4m-}$ type structures, rather than $[RSiO_{3/2}]$ type structures present in silsesquioxanes, and also exhibit many similarities to condensed silsesquioxane frameworks. For example, base-catalyzed equilibration of tetramethoxysilane, tetraethoxysilane, silicic acid, $SiO_2$, and combinations thereof can be equally well performed under conditions where the major Si— containing species in solution is $[Si_8O_{20}]^{8-}$.

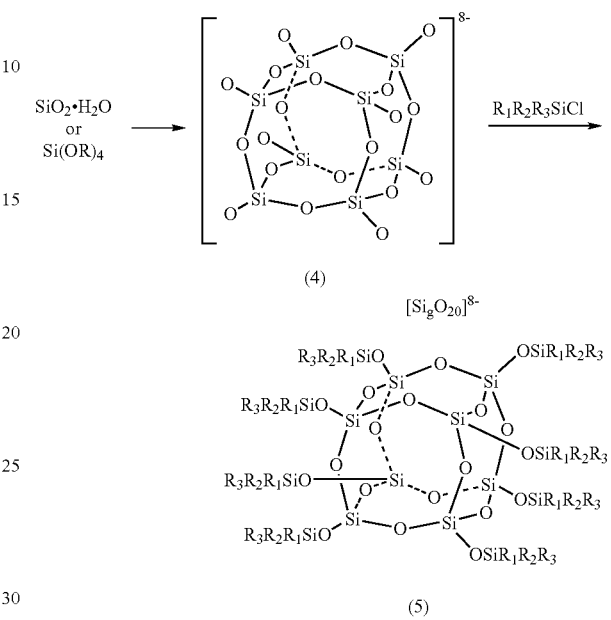

The hydrolysis of incompletely condensed polyhedral oligomeric silsesquioxane frameworks to fully condensed frameworks (i.e. $R_8Si_8O_{12}$) requires the formation of many intermediates. Usually, the intermediates are present in small amounts that are unstable under the reaction conditions, and are extremely difficult to isolate from a typical crude product mixture. However, the condensation of $RSiX_3$ occasionally produces very high yields of compounds that are logical intermediates to fully condensed silsesquioxane frameworks. The most widely used silsesquioxane framework is trisilanol (molecule 6a), which is obtained along with (c-$C_6H_{11}$)$_6Si_6O_9$ and molecule 7 via the hydrolytic condensation of (c-$C_6H_{11}$)$SiCl_3$. The synthesis of trisilanol (molecule 6a) is known to those skilled in the art and usually requires a gestation period of about 3 weeks to about 6 weeks to provide useful quantities. A cyclopentyl substituted trisilanol (molecule 6b) is also prepared in a similar manner and reaction times are greatly reduced by performing the reaction at elevated temperatures. The hydrolytic condensation of (c-$C_7H_{13}$)$SiCl_3$ and (norbornyl)$SiCl_3$ provide tetrasilanol (molecules 8a and 8b). These structures are known to those skilled in the art.

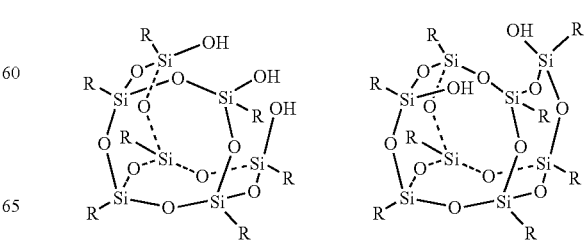

-continued

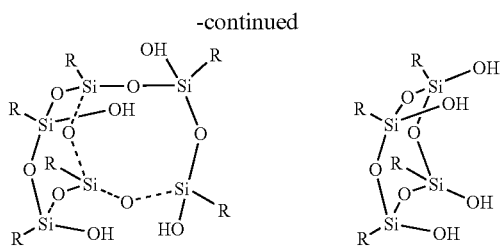

6a R=c-$C_6H_{11}$ 7 R=c-$C_6H_{11}$ 8a R=c-$C_7H_{13}$ 9 6b R=c-$C_5H_9$
8b R=norbornyl

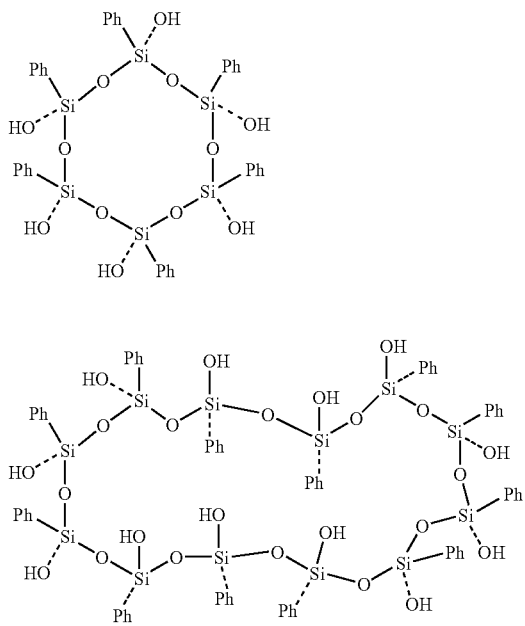

all cis (10)

tris(cis)-trans-tris(cis)-trans-tris(cis)- (11)

Polyhedral oligomeric silsesquioxane frameworks are also synthesized synthetically. Examples are stated for the $Si_8O_{12}R_8$ (12) structure but the method of manufacture can be applied to other network structures with appropriate changes that are known to one skilled in the art.

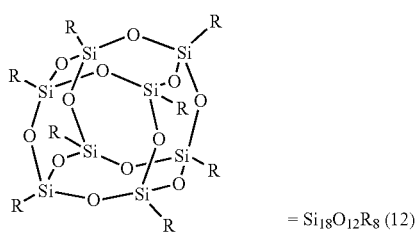

= $Si_{18}O_{12}R_8$ (12)

The R group on each molecule can be all identical but can also be different. R groups are selected from all known organic functional groups, including a hydride, an aliphatic-, an aromatic-, an alkyl-, an aryl-, an alkoxy-, a phenoxy-, partially or fully halogenated compounds, groups containing poylmerizable functionality, such as acrylates, epoxies, vinyl, hydroxyl, cyano, and combinations thereof.

A second aspect of the invention is a method of forming an optical film of the disclosed polycyclic or monocyclic perfluorovinyl compound. The method comprises providing a blend of monomer A and monomer B. Monomer A comprises a polycyclic or monocyclic perfluorovinyl compound that comprises at least one structural unit selected from the group consisting of formula I and formula II

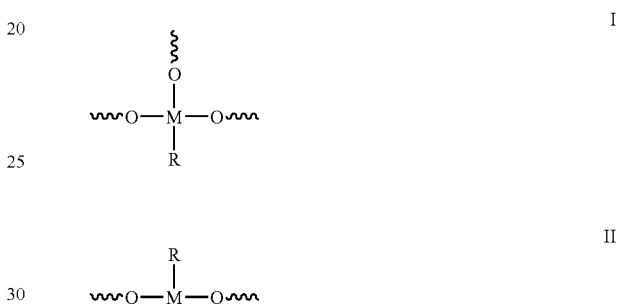

where M is independently at each occurrence a metal selected from group 14 of the periodic table of the elements and R is independently at each occurrence a bond, a hydrogen, an aliphatic group, a cycloaliphatic group, or an aromatic group; said polycyclic or monocyclic compound comprising at least two perfluorovinyl groups. Monomer B is an organic compound comprising at least two $CF_2$=CF— units. The method comprises providing the blend, mixing the blend with a photo-initiator and a photo-curable monomer C, where the photo-curable monomer C comprises at least one of an acrylate, an epoxy, a polyimide, a silicone, a vinyl compound, a carbonate, and a diene, to yield a mixed blend; partially polymerizing at least one of the blend and the mixed blend; depositing the mixed blend on a substrate to form a film; selectively exposing the film to radiation to at least partially polymerize monomer C; and curing the film so as to develop the final strength and adhesive properties in the disclosed optical film. Typically, curing comprises heating to a temperature of about 150° C. to about 300° C.

In more specific embodiments, M comprises at least one of silicon and germanium. In one embodiment, the polycyclic or monocyclic perfluorovinyl compound comprises a silicon-oxygen network. In another embodiment, the silicon-oxygen network comprises an oligomeric silsesquioxane. In another embodiment, the oligosilsesquioxane comprises a polyhedral oligomeric silsesquioxane. In another embodiment, the polyhedral oligomeric silsesquioxane comprises an octahedral structure. Various structural representations for the polycyclic or monocyclic perfluorovinyl compound are shown below.

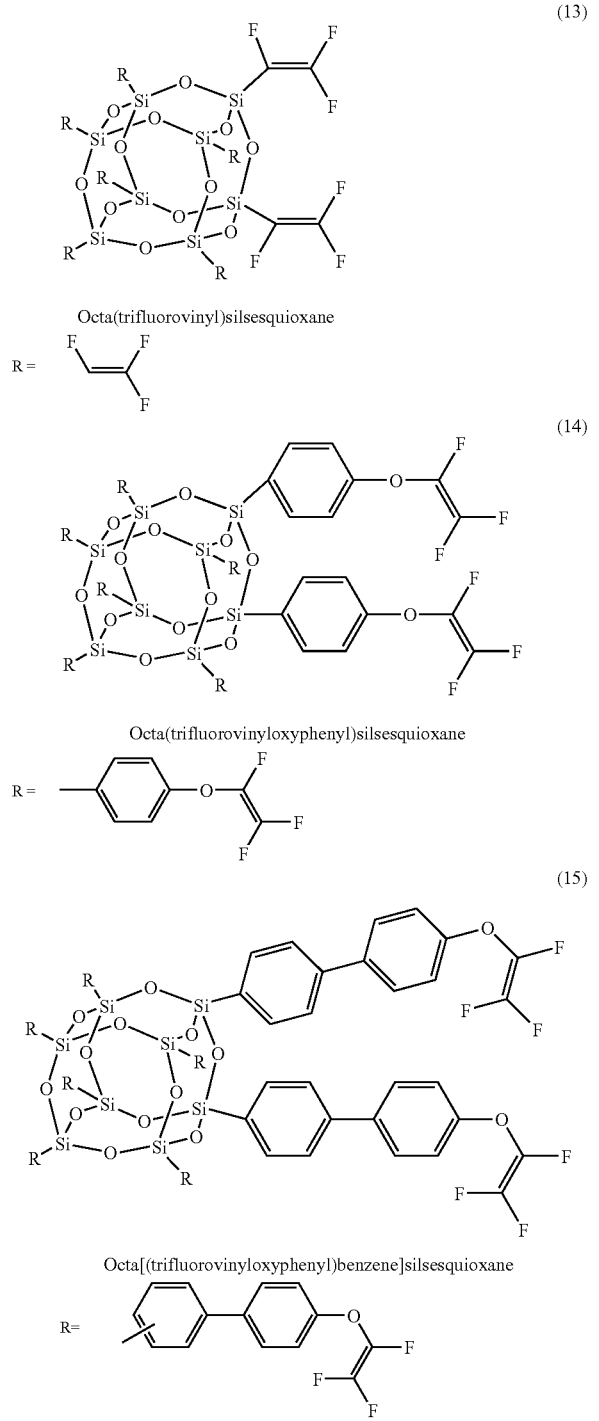

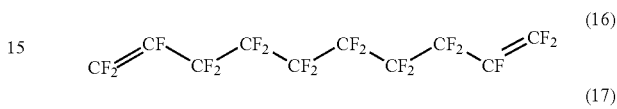

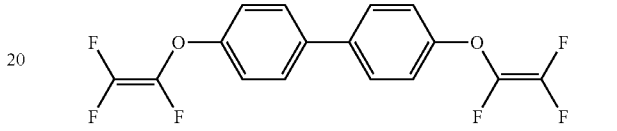

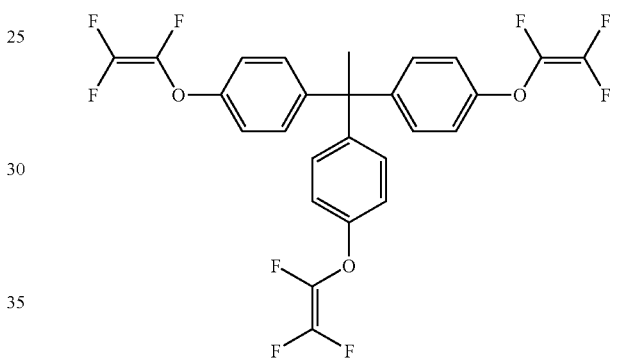

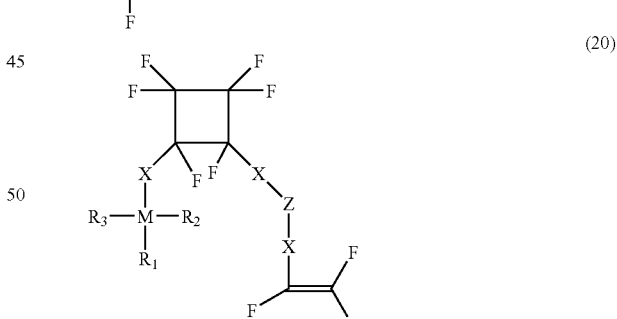

Monomer B, disclosed in the present invention, comprises a molecule represented by a $CF_2=CF-X_m-R-X_m-CF=CF_2$ type structure where X is independently at each occurrence a bond, an oxygen linkage, an amine linkage, a sulfur linkage, a silicon-containing linkage, an aliphatic group, a cycloaliphatic group, or an aromatic group, m is independently at each occurrence an integer from 0 to about 100, and R is a bond, an aliphatic group, a cycloaliphatic group, or an aromatic group. In one embodiment, monomer B comprises at least one of 1,6-di(trifluorovinyl)dodecafluorohexane (represented below as 16), 4,4'-bis(4-trifluorovinyl)oxy)biphenyl (represented as 17), 1,1,1-tris (4-trifluorovinyloxyphenyl)ethane (represented below as 18), bis(4-trifluorovinyl)oxy)perfluorobiphenyl (represented below as 19), and combinations thereof. Some of the listed molecules are commercially available, for instance, 4,4'-bis (4-trifluorovinyl)oxy)biphenyl (represented below as 17) and 1,1,1-tris(4-trifluorovinyloxyphenyl)ethane (represented below as 18) are available from Oakwood Products Inc., West Columbia, S.C. 29172. The non-limiting structural representations of Monomer B are represented by:

where structure 20 represents the partially cured polymer structure and Z is a molecule comprising all known organic functional groups, including R, a hydride, an aliphatic-, an aromatic-, an alkyl-, an aryl-, an alkoxy-, a phenoxy-, partially or fully halogenated compounds, groups containing poylmerizable functionality, such as acrylates, epoxies, vinyl, hydroxyl, cyano, and combinations thereof. Monomer B, when co-polymerized or blended with Monomer A, is typically used to obtain the desired material properties. In one embodiment, X comprises at least one O, N, S, Si, —CH$_2$—, —CF$_2$—, —CR$_2$—, alkyl group, alkoxy group, partially halogenated aliphatic group, or fully halogenated aliphatic group, and combinations thereof, wherein R is defined as in formula I.

In one embodiment of the present invention, the step of partially polymerizing at least one of the blend and the mixed blend comprises the partial polymerization of the blend of monomers A and B such that the partial polymerization is carried out prior to formation of the mixed blend. In another embodiment, the step of curing is carried out by at least one of heat radiation, light exposure and combinations thereof. In a third embodiment, the step of partially polymerizing at least one of the blend and the mixed blend comprises heating the blend for between about 2 minutes and about 60 minutes at a temperature between about 100° C. and about 200° C. In a fourth embodiment, the step of selectively exposing the film to radiation to at least partially polymerize monomer C further comprises diffusing monomer C from an unexposed area into an exposed area of the film after selectively exposing the film to radiation and in some embodiments, is done using a photo-mask. Typically, the steps of selectively exposing and diffusing are performed to generate a desired contrast (or gradient) in the index of optical refraction between the exposed and unexposed areas of the film. In a fifth embodiment, the mixed blend has a viscosity of about 10 CentiStokes (cSt) to about 10,000 CentiStokes (cSt). In a sixth embodiment, the mixed blend is deposited on a substrate comprising at least one of a metal, ceramic, glass, plastic, organic material, inorganic material, semiconductor, electronic device, micro-electromechanical system (MEMS) device, a sensor, a refractive index modulating device, a splitter, and combinations thereof. In a seventh embodiment, the mixed blend is deposited on the substrate using a technique comprising at least one of spin-coating, doctor-blading, dip-coating, casting, extrusion and combinations thereof.

The disclosed method of forming an optical film is equally applicable to the forming of an optical material and particularly to the development of a graded optical material. An optical material is used herein to mean a material having desired light transmission properties. A graded optical material is used herein to mean that the material has a structural heterogeneity in its properties across one of its dimensions. The optical path between the two extremities in the material may run along the length, breadth or height dimension within the material. Graded optical materials usually have controlled refractive indices in their bulk that enable an optical signal to turn through desired contours. It is hence desirable to have an optical waveguide that comprises a graded optical material. In another embodiment, the optically graded material has a refractive index between about 1.0 and about 2.42. In a third embodiment, the optically graded material provided by the disclosed method, has an optical loss of less than about 1 dB/cm in the wavelength range from about 600 nm to about 1600 nm and more specifically less than 0.1 dB/cm at wavelengths of about 850 nm, 1310 nm and 1550 nm and even more specifically, less than about 0.05 dB/cm at wavelengths of about 850 nm, 1310 nm and 1550 nm.

Polymers fabricated by the disclosed method have a high adhesion to a substrate. High adhesion is used herein to mean that a stack fabricated from different materials that are bonded together to form a structural unit remains intact without showing physical separation into individual layers under normal environmental changes or expected stress loads. Adhesion is typically tested by a variety of methods including scratch, peel, pull, blister and indentation testing, wherein the interface is subjected to very high stress levels and to consequent inhomogeneous deformation. For example, a standard test method for measuring adhesion by tape test is described by American Standard Test Method (ASTM) D3359 that classifies adhesion test results into 5 categories, with a test result of 5 indicating the highest measurable adhesion. The disclosed substrate typically comprises at least one of a metal, ceramic, glass, plastic, organic material, inorganic material, semiconductor, electronic device, micro-electromechanical system (MEMS) device, a sensor, a refractive index modulating device, a splitter, and combinations thereof. The disclosed polymer has a high adhesion to plastic, glass or silicon substrates of better than class 3B and more preferably better than class 4B according to the ASTM standard.

In one embodiment, the disclosed compound is a flame retardant. A flame retardant is generally known as a material that delays ignition and reduces the spread of a flame along its surface. In another embodiment, the compound has high thermal stability. A high thermal stability implies minimal or no change in desired properties when the material is exposed to temperatures of about 100° C. for an extended period of time. Thermally stable materials are defined as materials that retain their thermo-gravimetric and chemical integrity over a high temperature range and a temperature stability up to about 250° C. is preferable.

Polymers fabricated from the disclosed compound are attractive candidates for optical lenses, focusing devices, and systems or materials designed to confine and direct light waves in a direction determined by the physical boundaries of the systems or materials i.e. in optical waveguides.

A film made according to the disclosed method comprises a polymer fabricated from a concentration of monomer A of about 1% by weight to about 100% by weight and a concentration of monomer B of about 99% by weight to about 0% by weight. In the disclosed method, monomer A and monomer B, on blending, provide the desired material properties such as refractive index, adhesion, and fracture resistance, for example. In one embodiment, precursor blending is performed by mixing monomer A and monomer B in a round bottomed flask and stirring the mix with a magnetic stirrer. In some embodiments, monomer A and monomer B chemically react to provide a modified precursor. In other embodiments, monomer A and monomer B physically interact to provide a physically blended mix. In one embodiment of the invention, a chemically modified precursor obtained on blending monomer A and monomer B yields another monomer A for further processing. Blending monomer A and monomer B provides a method by which a comparatively low molecular weight polymer is used to provide a higher molecular weight polymer by polymer chain extension or cross-linking mechanisms or both. The provision of a modified precursor is referred to in the art as pre-polymerization. In some embodiments, monomer A and monomer B are blended and pre-polymerized in the presence of common organic solvents known in the art. In many embodiments, pre-polymerization is performed to attain a solution of workable viscosity and various solvents including benzene, toluene, alcohols, ethers, esters and combinations thereof are employed therefore.

In some embodiments, the pre-polymerized blend is heated for about 2 minutes to about 60 minutes at a temperature between about 100° C. and about 200° C. Heating yields at least one of a precipitate or a pre-polymerized blend with controllable viscosity to aid disposing upon the substrate of choice. The precipitate can be isolated by at least one of filtration, centrifugation, chromatography and combinations thereof and used for disposing upon the substrate. The pre-polymerized blend has a viscosity of about 10 cSt to about 10,000 cSt.

In order to provide areas of different refractive indices in the materials, a photo-curable monomer C is mixed with the pre-polymerized blend. Curing is understood in the art to imply the process of polymerizing a monomer or oligomer or cross-linking an existing polymer to attain its ultimate physical, chemical, mechanical and optical properties. As previously stated, photo-curable monomer C comprises at least one of an acrylate, an epoxy, a polyimide, a silicone, a vinyl, a carbonate, a diene, and combinations thereof to yield a mixed blend.

In some embodiments, a photo-initiator is added to the pre-polymerized blend. A photo-initiator is a compound that absorbs energy, directly or indirectly from photons to form reactive species, radicals or ions, which initiate polymerization. The photo-initiator typically comprises at least one of dibromoethane, benzophenone, benzyl dimethyl ketal, 2-hydroxy-2-methylphenylpropane-1-one, 1-hydroxycyclohexylphenyl ketone, 2-methyl-1-[4-(methyl thio)phenyl]-2-morpholino-propan-1-one, phenylbis(2,4,6-trimethylbenzoyl) phosphine oxide, N-hydroxyphthalimide triflate, (4-benzoylbenzyl)trimethylammonium chloride, benzoin methyl ether, diphenyliodonium hexafluorophosphate, and combinations thereof. In some embodiments a sensitizer is additionally added to the pre-polymerized blends. A sensitizer is a compound that extends the wavelength response range of the photo-initiator system and preferred sensitizers include at least one of 2,4-(bis(4-diethylaminobenzylidene) cyclopentanone (known commonly as DEAW), 2,4(bis-julolidenyl)cyclopentanone (known commonly as JAW), camphorquinone (known commonly as CQ), methyl benzoyl formate (known commonly as MBF), and combinations thereof.

Partial polymerization is carried out on at least one of the blend and the mixed blend. In one embodiment, partial polymerization occurs by partially polymerizing the blend before mixing. In a second embodiment, partial polymerization occurs after mixing of some or all of the constituents.

The pre-polymerized and mixed blend is deposited as a film on the substrate of choice using a technique comprising at least one of spin-coating, doctor blading, dip-coating, casting, extrusion, and combinations thereof. The substrate comprises at least one of a metal, ceramic, glass, plastic, organic material, inorganic material, semiconductor, electronic device, microelectromechanical system (MEMS) device, sensor, refractive index modulating device, a splitter, and combinations thereof.

The deposited film is subsequently exposed to radiation to at least partially polymerize monomer C. Selectively exposing the deposited film provides for diffusion of monomer C from the unexposed areas of the deposited film to the exposed areas of the deposited film hence yielding a material with graded properties. In one embodiment, the film is exposed to light of suitable wavelength using a photo-mask. In another embodiment, the entire film is exposed to radiation and no photo-mask is used. In a third embodiment, the selective exposing and diffusing are performed to generate a desired contrast in index of refraction between the exposed and unexposed areas of film thus providing a graded optical material.

The deposited blend is completely polymerized by the application of at least one of thermal energy and light energy. The step of applying thermal energy comprises heating the substrate to a temperature of about 150° C. to about 300° C., for example. The ultimate physical, chemical, mechanical and optical properties of the film are obtained on curing. In another embodiment, the film is exposed for about 2 minutes to about 60 minutes at a temperature between about 100° C. and about 200° C.

Stoichiometrically, each of monomer A and monomer B undergoes a chemical addition reaction by a 2+2 cyclo-addition mechanism to yield a product with a cyclic ring structure. In one embodiment of the present invention, a cyclo-butane ring structure is obtained. Using more complex and higher monomer A and monomer B, multiple and networked cyclic ring structures are obtained. In one embodiment, several cyclobutane ring structures are obtained in three-dimensional space.

Silicon-oxygen cage type networks reduce the chemical bonds that lead to vibrational overtone absorption at the desired wavelength. Such bonds are mainly X—H linkages where X comprises at least one of C, O, N, and other elements. The disclosed fluorinated silsesquioxane (when used as Monomer A) has no such bonds. By using a cyclic structure, a good control over end-groups and improved material properties are achieved. The cross-linking group is further, uniquely suitable for waveguide materials, since the reaction is catalyst-free and produces no X—H containing subgroups. The adjustment of properties, such as refractive index, toughness, $T_g$ and other optical, mechanical and holographic properties are made by selecting a spacer between the Si atom and the cross-linking group. In one embodiment, a phenyl group is used due to low C—H content and high stability. Additional property adjustments are made by mixing a different highly fluorinated monomer with at least two trifluorovinyl groups into the silsesquioxane monomers followed by co-polymerization. In one embodiment of the present invention, where photo-patterning is desired, a highly fluorinated photo-sensitive monomer is added to a partially polymerized silsesquioxane matrix and cross-linked upon exposure, followed by a complete polymerization achieved by the application of thermal energy.

Structurally, the use of a silica matrix via a silsesquioxane core decreases the total number of C—H and C—F bonds. One embodiment of the invention provides a compound with a lower optical loss from absorption by decreasing the number of C—H bonds. A second embodiment of the invention improves adhesion to a substrate by decreasing the number of C—F linkages. A third embodiment of the invention improves thermal stability by substituting C—X linkages with Si—O linkages.

A third aspect of the invention is an electro-optical device comprising a polymer fabricated from a polycyclic or monocyclic perfluorovinyl compound comprising at least one structural unit selected from the group consisting of formula I and formula II

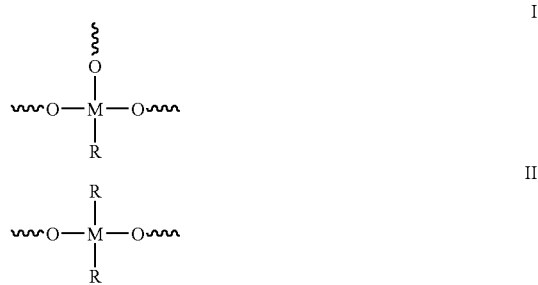

where M is independently at each occurrence a metal selected from group 14 of the periodic table of the elements; and R is independently at each occurrence a bond, a hydrogen, an aliphatic group, a cycloaliphatic group, or an aromatic group. The polycyclic or monocyclic compound comprises at least two perfluorovinyl groups.

In one embodiment, the electro-active component of the disclosed electro-optical device comprises at least one of an organic light-emitting diode, a photovoltaic cell, a light emitting diode, an electro-luminescent material, a cathodoluminescent material, a phosphorescent material, a mirror, a laser, an optical fiber, a MEMS device, a device for concentrating or dissipating light, a waveguiding device, a splitter, and combinations thereof. In another embodiment, the electro-optical device is configured to be exercisable by a power source.

A fourth aspect of the invention is a polymer prepared by reacting components (a), (b) and (c) wherein component (a) is a blend of monomer A and monomer B, said monomer A comprising a polycyclic or monocyclic perfluorovinyl compound comprising at least one structural unit selected from the group consisting of formula I and formula II

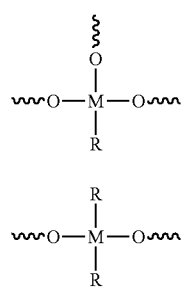

where M is independently at each occurrence a metal selected from group 14 of the periodic table of the elements, R is independently at each occurrence a bond, a hydrogen, an aliphatic group, a cycloaliphatic group, or an aromatic group. The polycyclic or monocyclic compound comprises at least two perfluorovinyl groups, monomer B is an organic compound comprising at least two $CF_2=CF-$ units, component (b) is at least one photo-curable monomer C, wherein the photo-curable monomer comprises at least one of an acrylate, an epoxy, a polyimide, a silicone, a vinyl, a carbonate, a diene, and combinations thereof and component (c) is at least one photo-initiator.

In one embodiment of the present invention, the photo-initiator comprises at least one of dibromoethane, benzophenone, benzyl dimethyl ketal, 2-hydroxy-2-methyl-phenyl-propane-1-one, 1-hydroxy cyclohexyl phenyl ketone, 2-methyl-1-[4-(methyl thio)phenyl]-2-morpholino-propan-1-one, phenylbis(2,4,6-trimethylbenzoyl)phosphine oxide, N-hydroxyphthalimide triflate, (4-Benzoylbenzyl)trimethylammonium chloride, benzoin methyl ether, diphenyliodonium hexafluorophosphate, and combinations thereof.

The following examples are included to illustrate the various features and advantages of the present invention, and are not intended to limit the invention.

EXAMPLE 1

Preparation of 4-Bromophenyltrichlorosilane Using Tetrachlorosilane

Freshly activated magnesium (8.5 g, 0.35 mol) was slowly added over a period of four hours to a solution of 1,4-dibromobenzene (80 g, 0.34 mol) in 200 mL of diethylether, keeping the temperature below 30° C. The reaction mixture was stirred for 8 hours and then slowly added to a mixture of tetrachlorosilane (100 mL, 0.87 mol) in diethylether (50 mL) within 12 hours. The mixture was stirred for 12 hours, and unreacted tetrachlorosilane and diethylether were removed in vacuum. The remaining liquid was fractionally distilled through a Vigreux column under reduced pressure to provide 4-bromophenyltrichlorosilane as an oil (350 μHg/85° C.-37 g/37%). $^1$HNMR(400 MHz, CDCl$_3$): δ 7.69 (4H, dd). $^{13}$CNMR (100 MHz, CDCl$_3$): δ 134.6, 131.9, 130.4, 128.2. GC-MS: 290 (M+).

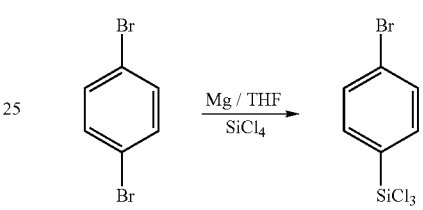

EXAMPLE 2

Preparation of 4-Bromophenyltriethoxysilane Using tetraethoxysilane

Freshly activated magnesium (8.5 g, 0.35 mol) was slowly added over a period of four hours to a solution of 1,4-dibromobenzene (80 g, 0.34 mol) in 200 mL of diethylether, keeping the temperature below 30° C. The reaction mixture was stirred for 8 h and then slowly added to a mixture of tetraethoxysilane (100 mL, 0.44 mol) in Et$_2$O (50 mL). The mixture was stirred for 12 h, and unreacted tetraethoxysilane and diethylether were removed in vacuum. The remaining liquid was fractionally distilled through a Vigreux column under reduced pressure to provide 4-bromophenyltriethoxysilane as a clear oil (37 g, 37%, bp 80–90° C. at 250 μHg). $^1$HNMR(400 MHz, CDCl$_3$): δ 7.56 (4H, dd), 3.89 (6H, q), 1.27 (9H, t). $^{13}$CNMR (100 MHz, CDCl$_3$): δ 136.4, 131.1, 58.8, 18.2. GC-MS: 318 (M+).

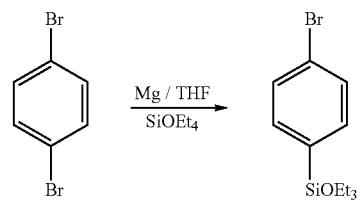

EXAMPLE 3

Preparation of Octa(4-Bromophenyl)silsesquioxane

4-Bromophenyltrichlorosilane (29 g, 0.1 mole) is dissolved in 200 mL of methanol and 20 ml water and refluxed for 36 hrs. The liquid is decanted from the gel and the gel is sonicated in methanol to yield a white powder. Filtration and column chromatography are used to purify the product i.e. Octa(4-bromophenyl)silsesquioxane.

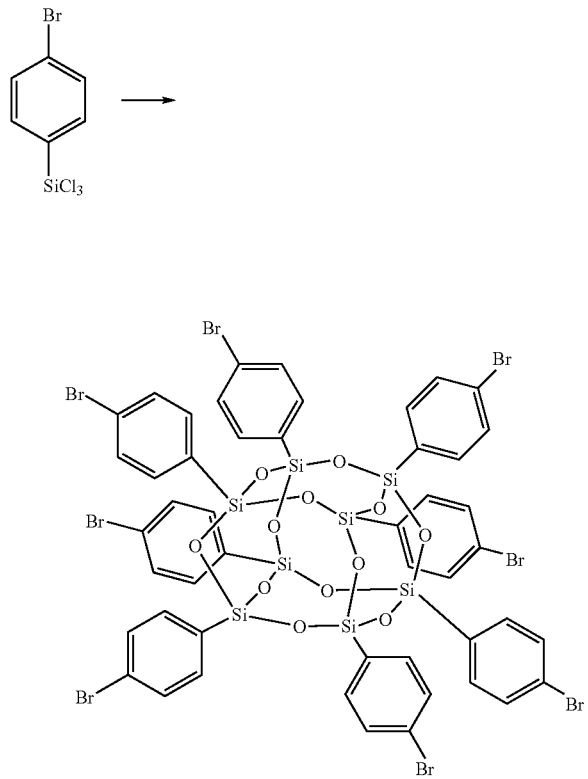

EXAMPLE 4

Preparation of 1-(trifluorovinyloxy)-4-[4,4,5,5-tetramethyl-1,3,2-dioxaborolane]benzene 1-Bromo-4-(trifluorovinyloxy)benzene commercially available from Oakwood Products, Inc. was used as precursor. 12.65 g (0.05 mol) of 1-Bromo-4-(trifluorovinyloxy) benzene in 100 mL THF (tetrahydrofuran) was added dropwise to 2.5 g (0.1 mole) of freshly activated magnesium in 100 mL THF in a 500 mL 3-neck flask equipped with an addition funnel, a thermometer, a stirrer and a nitrogen inlet. The temperature was kept below 30° C. during the addition. After complete conversion to a Grignard intermediate, the solution was added dropwise to 10.2 g (1.1 equivalents) of 2-Isopropoxy-4,4,5,5-tetramethyl-1,3,2-dioxaborolane in 50 mL THF at room temperature. The solution was refluxed for 12 hours, diluted with water, extracted with dichloromethane, dried over $MgSO_4$ and concentrated. Fractionated distillation yielded at 300 μHg and 100° C. the desired product as a clear oil in 37% provision. $^1$HNMR(400 MHz, acetone-$d_6$): δ 7.83 (2H, dd), 7.22 (2H, dd), 1.34 (12H). $^{13}$CNMR (100 MHz, acetone-$d_6$): δ 205.1, 154.2, 147 (m), 136.9, 133 (m), 114.92, 83.8, 24.3. $^{19}$FNMR (470 MHz, acetone-$d_6$): δ −123.85 (t), −130.8 (t), −138.3 (t). GC-MS: 300 (M+).

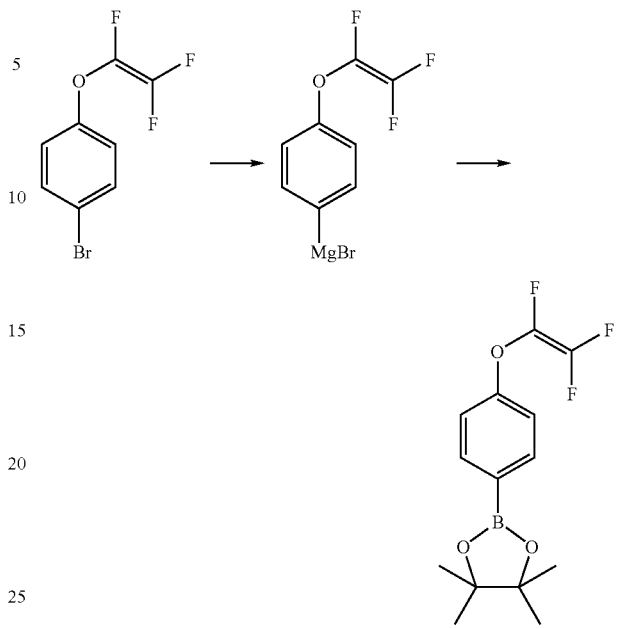

EXAMPLE 5

Preparation of Octa[4-trifluorovinyloxyphenyl)benzene]silsesquioxane

To a 100 mL 3-neck round bottom with 50 mL toluene, 10 mL $Na_2CO_3$ and 2 mL ethanol are added 1 g of octa(4-bromophenyl)silsesquioxane, eight equivalents of 1-(trifluorovinyloxy)-4-[4,4,5,5-tetramethyl-1,3,2-dioxaborolane] benzene and 0.5 equivalents of Tetrakis(triphenylphosphine) palladium(0) under a nitrogen blanket. The mixture is stirred for 24 hrs, cooled to room temperature and washed with two times 100 mL water. The toluene phase is dried over $MgSO_4$, filtered, concentrated and the product is precipitated into methanol as a white powder. 19F-NMR (470 MHz) δ −122.96 (dd, 1F), −129.9 (dd, 1F), −137.39 (dd, 1F).

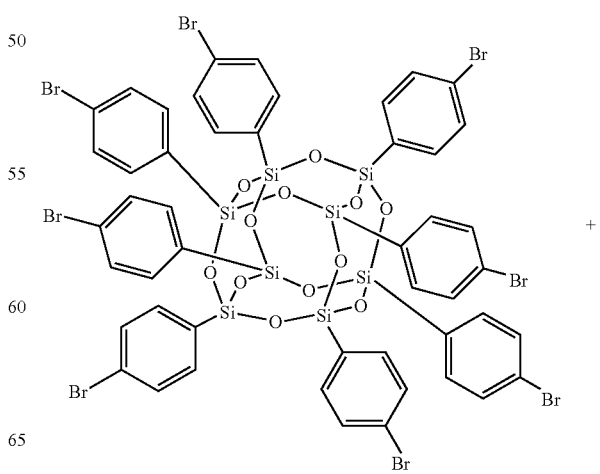

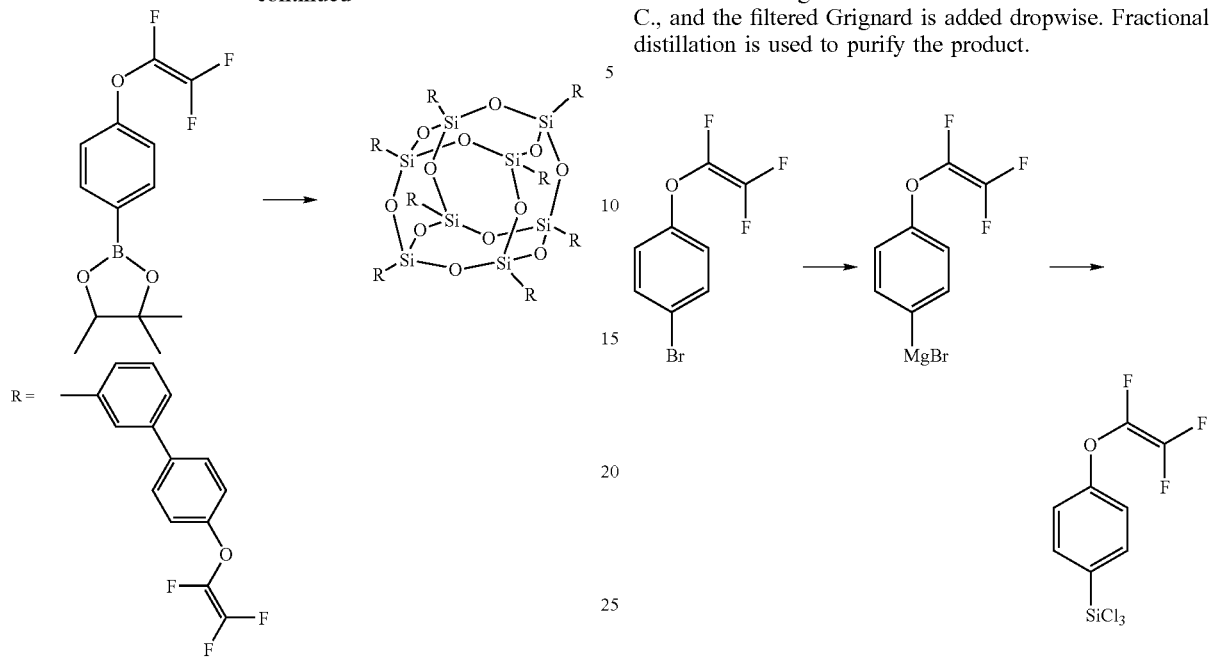

EXAMPLE 6

Preparation of Trifluorovinyl triethoxysilane

A dry 3-neck round bottom flask with nitrogen and stir-bar is charged with approximately (9.5 mL, 14.5 g at −78° C., 0.12 mol) iodotrifluoroethylene and 200 mL diethylether pre-cooled to −78° C. Sec-butyl lithium (89 mL, 1.4 M solution, 0.12 mol) is added dropwise over 1 hour. Solution is allowed to stir for 5 minutes at −78° C. Chlorotriethoxysilane (24.35 mL, 0.12 mol) is added over 5 minutes at −78° C. The solution is allowed to warm slowly and allowed to stir overnight. A clear yellow solution remains. Fractional distillation is used to purify the product.

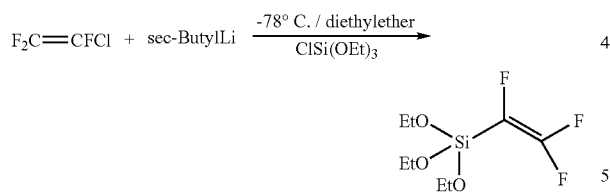

EXAMPLE 7

Preparation of (4-trifluorovinyloxyphenyl)trichlorosilane

A 3-neck round bottom flask with nitrogen and stirbar is loaded with activated magnesium (7 g, 0.288 mol) shavings. After cooling, the flask is fitted with a condenser, and 200 mL of dry ether and 2 crystals of iodine is added. One-third of the 4-trifluovinylether-1-bromobenzene (total used, 10 g, 0.0.039 mol) is added. Once started, the remaining 4-trifluovinylether-1-bromobenzene is added. The solution turns brown slowly, and the temperature is kept below 25° C. A slight excess of tetrachlorosilane (SiCl$_4$) in 100 mL tetrahydrofuran is transferred to a 1000 mL 3-neck flask with stir-bar and nitrogen blanket. The solution is cooled to 20° C., and the filtered Grignard is added dropwise. Fractional distillation is used to purify the product.

EXAMPLE 8

Preparation of Octa(4-Trifluorovinyloxyphenyl)silsesquioxane

4-Trifluorovinyloxyphenyltrichlorosilane (31 g, 0.1 mole) is dissolved in 200 mL of methanol and 20 ml water and refluxed for 36 hrs. The liquid is decanted from the gel and the gel is sonicated in methanol to yield a white powder. Filtration and column chromatography are used to purify the product Octa(4-trifluorovinyloxyphenyl)silsesquioxane.

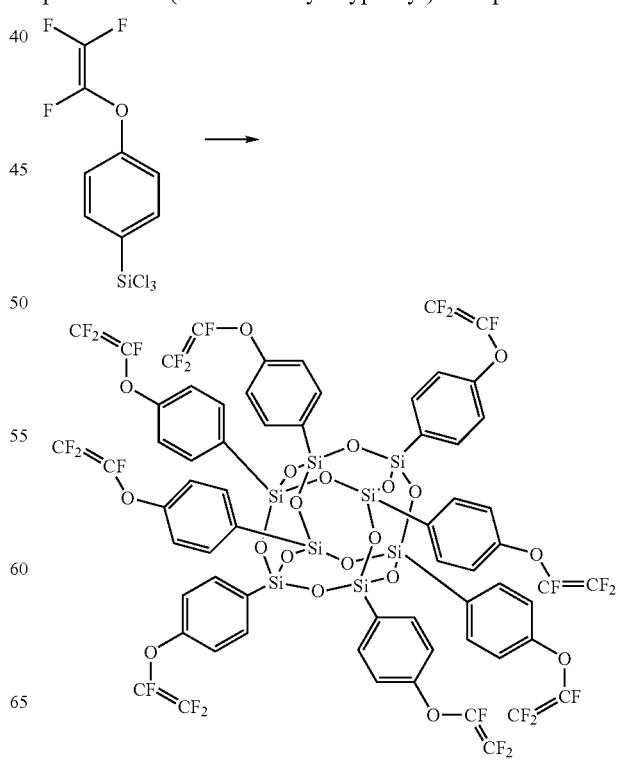

EXAMPLE 9

Preparation of 2-(triethoxysilane)tetrafluoroethyl trifluorovinyl ether

A 3-neck round bottom flask with nitrogen and stirbar is loaded with activated magnesium (7 g, 0.288 mol) shavings. After cooling, the flask is fitted with a condenser, and 200 mL of dry ether and 2 crystals of iodine are added. One-third of the 2-bromotetrafluoroethyl trifluorovinyl ether (total used, 58 g, 0.209 mol) is added. At least 1 mL of dibromoethane is added to initiate the Grignard. Once started, the remaining 2-bromotetrafluoroethyl trifluorovinyl ether is added. The solution is heated for 3 days under nitrogen, cooled, air-free filtered and used immediately, by adding one of the three following materials: tetraethoxysilane, tetrachlorosilane, or chlorotriethoxysilane in slight excess. Fractional distillation is used to purify the product.

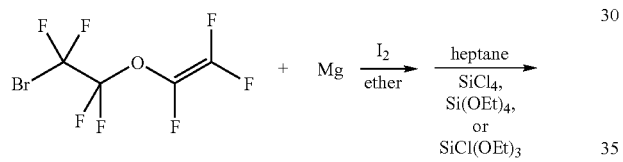

EXAMPLE 10

Preparation of Octa[tetrafluoroethyl trifluorovinyl ether]silsesquioxane 2-(triethoxysilane)tetrafluoroethyl trifluorovinyl ether is dissolved in 200 mL of methanol and 20 ml water and refluxed for 36 hrs. The liquid is decanted from the gel and the gel is sonicated in methanol to yield a white powder. Filtration and column chromatography are used to purify the product Octa[tetrafluoroethyl trifluorovinyl ether]silsesquioxane.

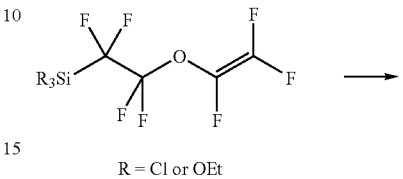

R = Cl or OEt

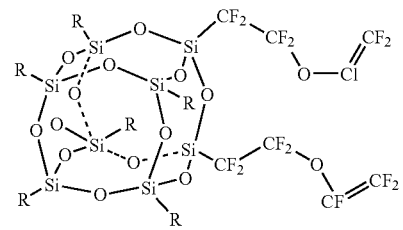

EXAMPLE 11

Polymerization of Octa[4-trifluorovinyloxyphenyl)benzene]silsesquioxane

The monomer Octa[4-trifluorovinyloxyphenyl)benzene]silsesquioxane is placed in a 1 liter 3-neck flask with 250 ml of perfluorotetradecahydrophenanthrene, mechanically stirred and heated under a nitrogen atmosphere to reflux. After about 3 hours the formed polymer precipitates. The cooled polymer is removed from the flask and dried under high vacuum.

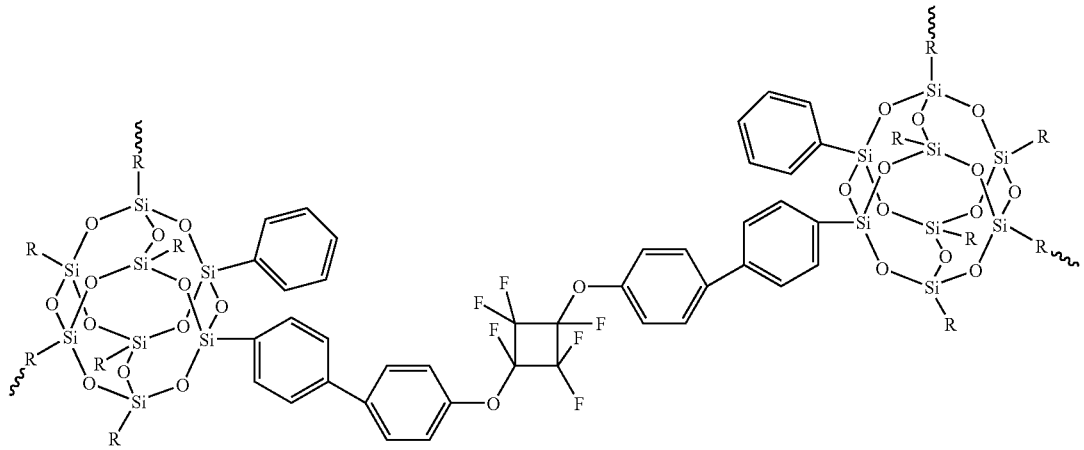

EXAMPLE 12

Copolymerization of Octa[4-trifluorovinyloxyphenyl)benzene]silsesquioxane and 1,6-Divinyldodecafluorohexane The monomers octa[4-trifluorovinyloxyphenyl)benzene]silsesquioxane and 1,6-Divinyldodecafluorohexane are sealed in a quartz ampule with 25 mL of perfluoroteradecahydrophenanthrene and heated to 250° C. in a high-pressure apparatus. After about 5 hours the reaction mixture is cooled and the formed polymer precipitates. The cooled polymer is removed from the flask and dried under high vacuum.

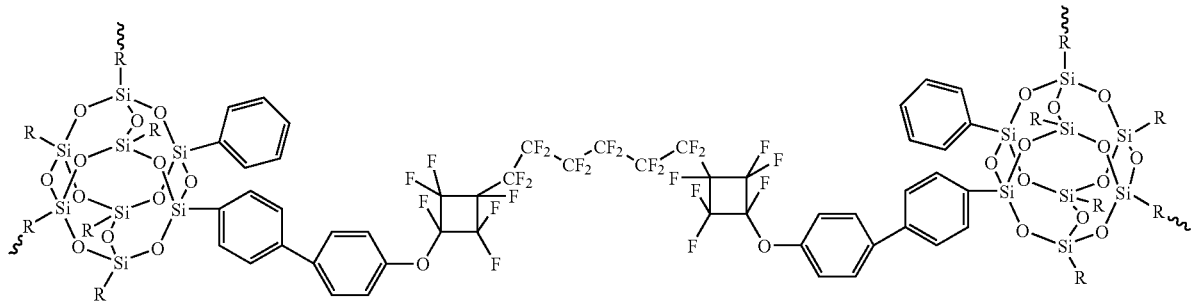

While typical embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

What is claimed is:

1. A method of forming an optical film, said method comprising:
   (a) providing a blend of monomer A and monomer B, said monomer A comprising a polycyclic or monocyclic perfluorovinyl compound comprising at least one structural unit selected from the group consisting of formula I and formula II

-continued

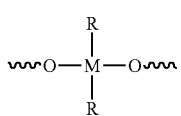

wherein M is independently at each occurrence a metal selected from group 14 of the periodic table of the elements, R is independently at each occurrence a bond, a hydrogen, an aliphatic group, a cycloaliphatic group, or an aromatic group; said polycyclic or monocyclic compound comprising at least two perfluorovinyl groups, said monomer B being an organic compound comprising at least two $CF_2=CF-$ units;

(b) mixing said blend with a photo-initiator and a photo-curable monomer C, wherein said photo-curable monomer C comprises at least one of an acrylate, an epoxy, a polyimide, a silicone, a vinyl compound, a carbonate, and a diene, to yield a mixed blend;

(c) partially polymerizing at least one of the blend and the mixed blend;

(d) depositing said mixed blend on a substrate to form a film;

(e) selectively exposing said film to radiation to at least partially polymerize monomer C; and (f) curing said film.

2. The method according to claim 1, wherein said M comprises at least one of silicon and germanium.

3. The method according to claim 1 wherein said polycyclic or monocyclic perfluorovinyl compound comprises a silicon-oxygen network.

4. The method according to claim 3 wherein said silicon-oxygen network comprises an oligomeric silsesquioxane.

5. The method according to claim 4, wherein said oligomeric silsesquioxane comprises a polyhedral oligosilsesquioxane.

6. The method according to claim 5, wherein said polyhedral oligomeric silsesquioxane comprises an octahedral structure.

7. The method according to claim 1, wherein said monomer B further comprises $CF_2=CF-X_m-R-X_m-CF=CF_2$ wherein X is independently at each occurrence a bond, an oxygen linkage, an amine linkage, a sulfur linkage, a silicon-containing linkage, an aliphatic group, a cycloaliphatic group, or an aromatic group, m is independently at each occurrence an integer from 0 to about 100, and R is a bond, an aliphatic group, a cycloaliphatic group, or an aromatic group.

8. The method according to claim 7 wherein X comprises at least one O, N, S, Si, $-CH_2-$, $-CF_2-$, $-CR_2-$, alkyl group, alkoxy group, partially halogenated aliphatic group, or fully halogenated aliphatic group, wherein R is a bond, an aliphatic group, a cycloaliphatic group, or an aromatic group.

9. The method according to claim 1, wherein (c) comprises the partial polymerization of the blend of monomers A and B, said partial polymerizing being carried out prior to formation of the mixed blend.

10. The method according to claim 1, wherein said curing in (f) is carried out by at least one of heat radiation, light exposure and combinations thereof.

11. The method according to claim 1, wherein (c) comprises heating said blend for between about 2 minutes and about 60 minutes at a temperature between about 100° C. and about 200° C.

12. The method according to claim 1, wherein (e) further comprises diffusing monomer C from an unexposed area into an exposed area of said film after selectively exposing said film to radiation.

13. The method according to claim 12 wherein selectively exposing and diffusing are performed to generate a desired contrast in index of refraction between exposed and unexposed areas of said film.

14. The method according to claim 1, wherein said mixed blend has a viscosity of about 10 cSt to about 10,000 cSt.

15. The method according to claim 1, wherein said mixed blend is deposited on a substrate using a technique comprising at least one of spin-coating, doctor blading, dip-coating, casting, extrusion and combinations thereof.

16. The method according to claim 1, wherein step (e) further comprises exposing said film to radiation using a photo-mask.

17. The method according to claim 10, wherein said curing comprises heating to a temperature of about 150° C. to about 300° C.

* * * * *